(12) United States Patent
Dedrick et al.

(10) Patent No.: US 7,861,723 B2
(45) Date of Patent: Jan. 4, 2011

(54) APPARATUS, SYSTEM AND METHOD FOR DETECTING AND TREATING AIRWAY OBSTRUCTIVE CONDITIONS DURING SLEEP

(75) Inventors: David L. Dedrick, 2379 NW. Todd's Crost Dr., Bend, OR (US) 97701; John Barney, Powell Butte, OR (US)

(73) Assignee: David L. Dedrick, Bend, OR (US)

( * ) Notice: Subject to any disclaimer, the term of this patent is extended or adjusted under 35 U.S.C. 154(b) by 291 days.

(21) Appl. No.: 12/156,860

(22) Filed: Jun. 3, 2008

(65) Prior Publication Data

US 2009/0293886 A1 Dec. 3, 2009

Related U.S. Application Data

(60) Provisional application No. 60/933,783, filed on Jun. 7, 2007.

(51) Int. Cl.
*A61F 5/56* (2006.01)
*A61F 11/00* (2006.01)
*H04R 25/00* (2006.01)

(52) U.S. Cl. ............... 128/848; 128/864; 128/865; 381/312; 381/328; 181/130

(58) Field of Classification Search ............ 128/848, 128/864–868; 381/312, 328, 329; 623/10, 623/23.67; 181/129–135
See application file for complete search history.

(56) References Cited

U.S. PATENT DOCUMENTS

| | | | |
|---|---|---|---|
| 6,256,396 B1 * | 7/2001 | Cushman | 381/328 |
| 2003/0199945 A1 | 10/2003 | Ciulla | |
| 2004/0215053 A1 * | 10/2004 | Jorgensen et al. | 600/25 |
| 2005/0197588 A1 | 9/2005 | Freeberg | |

OTHER PUBLICATIONS

International Search Report for Int'l Appl. No. PCT/US09/03266; Int'l Searching Authority; Jul. 16, 2009; 10 pages.

* cited by examiner

*Primary Examiner*—Patricia M Bianco
*Assistant Examiner*—Keri J Nicholson
(74) *Attorney, Agent, or Firm*—Ater Wynne LLP

(57) ABSTRACT

An airway obstruction correction apparatus including an expandable bladder configured to fit within a user's external auditory canal, a pump configured to expand the bladder with a pumped fluid, a passage coupled with the pump and with the bladder and configured to convey a fluid between the pump and the bladder, a microcontroller coupled with the pump and configured to affect an activation condition of the pump, and a reservoir coupled with the pump and configured to retain sufficient fluid to expand the bladder into contact with a surface of the auditory canal when transferred to the bladder by the pump. At least one of a local data processing means and/or a remotely located data processing means can be configured to receive data from the apparatus and transmit data to the apparatus via a data networking means and/or at least one of a wired or wireless signal. According to a method using an apparatus configured as described, a detected indication of an obstructed airway causes the apparatus to stimulate a user and induces an involuntary airway clearing response.

26 Claims, 9 Drawing Sheets

APPARATUS, SYSTEM AND METHOD FOR DETECTING AND TREATING AIRWAY OBSTRUCTIVE CONDITIONS DURING SLEEP

RELATED APPLICATIONS

This application claims the benefit of priority to Provisional Application No. 60/933,783 entitled APPARATUS, SYSTEM AND METHOD FOR DETECTING AND TREATING AIRWAY OBSTRUCTIVE CONDITIONS DURING SLEEP and filed on Jun. 7, 2007.

FIELD OF THE INVENTION

This invention relates generally to the field of treatment of sleep disorders. More particularly, it concerns an apparatus, system, and method for detecting, correcting, and preventing sleep apnea, snoring, and other airway obstructive conditions in sleeping persons.

BACKGROUND OF THE INVENTION

Obstructive sleep apnea, which involves an interruption of normal breathing during sleep, is a very serious condition associated with numerous detrimental health effects. The most common type of sleep apnea is fundamentally caused by a relaxation of the human upper airway muscles during periods of sleep. Particularly, the majority of obstructive airway events are precipitated by the tongue and jaw sagging backwards when all of the muscles of the body relax with sleep. In a fair percentage of the population, approximately 10-15 percent, such relaxation closes the airway sufficiently to substantially and/or completely preclude breathing. In other instances, the airway is only partially occluded, causing the sleeping person to work harder during breathing to obtain sufficient oxygen. The characteristic noises of snoring result from air being forcefully drawn into and/or forced out through the airway past an obstruction.

Both snoring and sleep apnea cause oxygen levels to drop, and cause sleep to become highly fractionated. Among other things, intermittent oxygen deprivation can lead to damage to the heart and brain, resulting in an increased risk and/or incidence of heart attack and stroke. At a minimum, mild sleep apnea and snoring result in non-restorative sleep and daytime sleepiness, which can further lead to a host of dangers resulting from a lack of awareness and adequate reaction speed (e.g., motor vehicle accidents, industrial accidents). Long term adherence to therapy, however, has been shown to reduce the risk of heart attack, stroke, death, and alertness related events such as motor vehicle accidents. The three primary accepted treatments and/or therapies for sleep apnea and snoring include Continuous Positive Airway Pressure (CPAP), Mandibular Advancement Devices (e.g., oral appliances), and surgery.

CPAP therapy involves using a mask-like device that provides a gentle amount of counter air pressure: through a snugly fitting mask worn about the nose during sleep. The air pressure provided by the mask, often conceived of as a "pneumatic splint", prevents the upper airway muscles from fully collapsing into the airway when relaxed. The device is highly effective, but due to a large number of disadvantages, adherence to CPAP therapy by patients can be as low as approximately 50 percent. Among the disadvantages are sometimes poorly fitting and/or leaking masks, claustrophobia experienced by some patients, awkwardness of the mask and tubing, and the noise produced by and space consumed by the typically nearby air compressor.

A mandibular advancement device functionally and structurally comprises a bite plate configured to hold the lower jaw (mandible) forward while one sleeps. This is particularly helpful for patients experiencing snoring and sleep apnea that occurs when sleeping supine (i.e., lying on their back and facing upward). However, long term use of a mandibular advancement device frequently causes jaw discomfort and migration of teeth in the jaw, both consequences of a constant force exerted upon the jaw for durations of up to 6-8 hours at a time (e.g., all night).

Surgical options for treating sleep apnea and snoring are numerous, but none provide a guaranteed cure except the drastic step of performing a tracheotomy. As substantial deterrents, surgeries are expensive, painful, and in the best of situations, provide cure rates of only approximately 50-70 percent. Further, surgery can lead to long-term complications such as altered swallowing, speech impairment, and scar tissue formation. In general, for patients having only mild sleep apnea and/or snoring, the awkwardness, discomfort, and risks of these three conventional forms of therapy frequently outweigh the potential benefits. Therefore, treatment in patients experiencing relatively mild symptoms is particularly problematic.

DETAILED DESCRIPTION OF THE PREFERRED EMBODIMENTS

The invention in accordance with a preferred embodiment involves an airway obstruction correction apparatus including generally a pair of expandable bladders configured to fit within a user's respective right and left external auditory canals. A pump is configured to expand the bladders with a fluid transferred through a passage coupled with the pump, the bladders and a fluid reservoir. A microcontroller is configured to recognize indications of an obstructed airway in the form of an electrical signal representative of data, and to affect an activation condition of the pump.

Embodiments further include at least one of a local and/or extended system including a data processing means configured to receive data from the apparatus and/or transmit data to the apparatus by at least one of a wired or wireless signal. According to a method of using an apparatus configured as described herein, a detected indication of an obstructed airway causes the apparatus automatically to stimulate a user and to induce an involuntary airway clearing response.

The embodiments of the invention are far more numerous and varied than can be described in summary, however, and therefore are set forth below in greater detail.

Airway Obstruction Correction Apparatus

Figure 1:
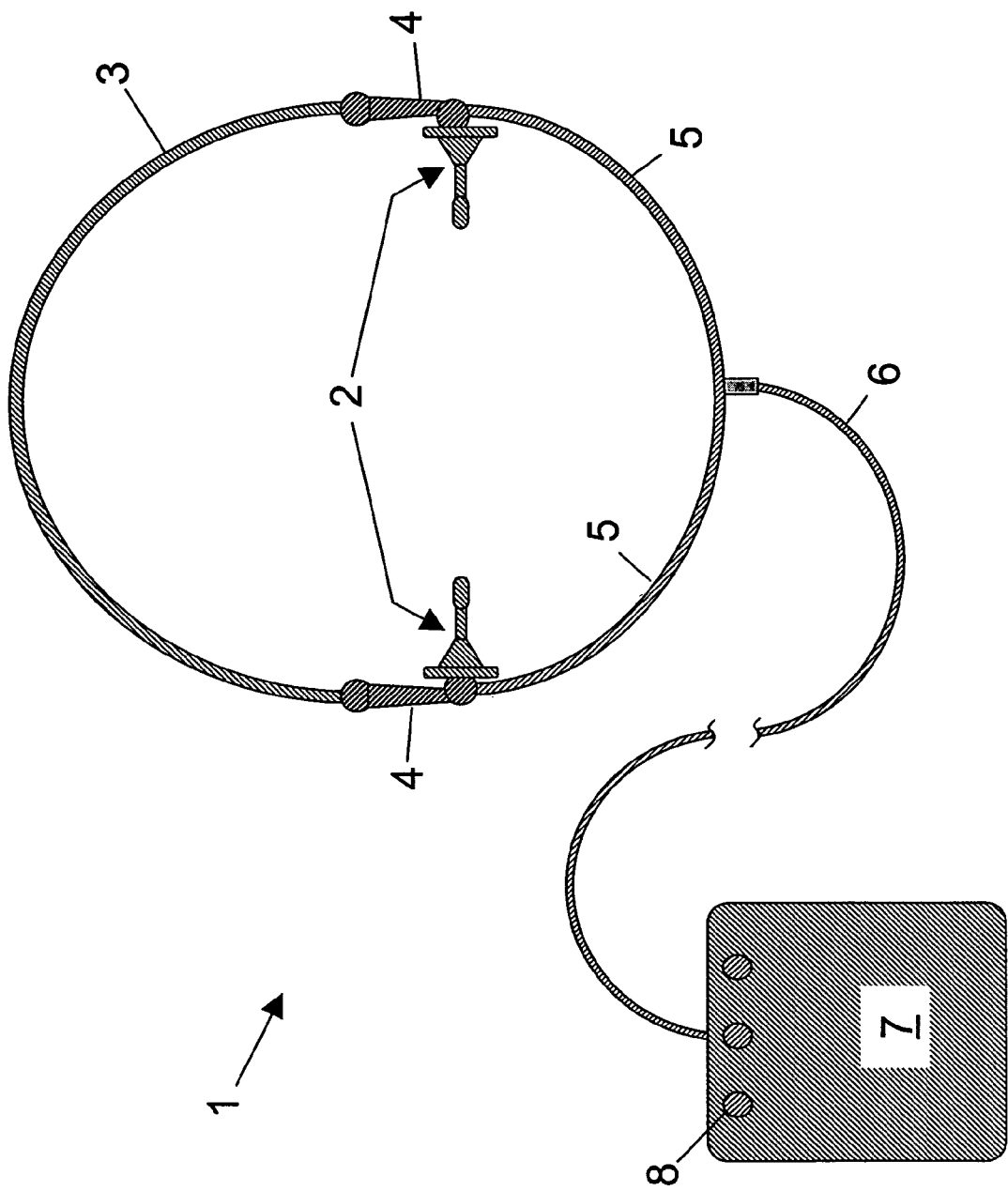
FIG. 1 depicts an airway obstruction correction apparatus according to an embodiment of the invention.

FIG. 1 depicts an airway obstruction correction apparatus 1 (hereinafter, apparatus) according to an embodiment of the invention. The apparatus 1 includes at least one, but more typically two, ear portion(s) 2 configured for insertion at least partially into the respective left and/or right auditory canals of a human subject (hereinafter, user). The ear portion(s) 2 are positioned proximate to opposing portions of a retention structure 3 configured to retain the ear portions 2 securely yet comfortably in position relative to a user's ear canal(s) while the user sleeps. Positioned intermediate between the retention structure 3 and an ear portion 2 in the depicted embodiment, and operatively coupled with each, is a positionally-adjustable connecting member 4 enabling the position of the ear portion 2 to be altered relative to the retention structure 3 and/or relative to a user's auditory canal.

Operatively coupled at one end with an ear portion is a relatively flexible passage 5 enabling transfer of a fluid to and from the ear portion 2. In embodiments, the passage is individually and operatively coupled at an opposite end with a pump. In the alternative embodiment depicted in FIG. 1, each respective right and left passage 5 is operatively coupled with an end of a common passage 6, and the opposing end of the common passage 6 is operatively coupled with a pump located for example within a control unit 7. Fluid transferred from the pump into common passage 6 is therefore conveyed to and through passages 5 to each respective ear portion 2. In a typical embodiment, the fluid is a liquid, for example a saline solution. A liquid fluid is generally not compressible, so provides accurate feedback regarding an actual level of force exerted within a user's auditory canal. According to alternative embodiments, however, a fluid can include a material in a gaseous state, such as air, nitrogen, or some other.

The pump, as well as numerous other components, are retained within a control unit 7 which may be worn or otherwise placed by the user separately from the wearable ear portions 2. Common passage 6 is also typically flexible, enabling variation in the position of the control unit 7 relative to the ear portions 2. Control unit 7, when configured for wearing by the user, will generally be dimensionally small and unobtrusive, without projecting or sharply angular external features. Therefore, the control unit is unlikely to irritate and/or rouse a sleeping user. The control unit will typically, although not exclusively, include one or more visible status indicators 8, to indicate an operational status and/or an error condition, for example. The cumulative lengths of the passages 5/6 establish how remotely the control unit 7 can be placed relative to the ear portions 2.

FIG. 1 depicts the general nature and arrangement of components of an apparatus 1 according to an embodiment of the invention, but not intended to imply or express limitations in the configuration, presence, or positioning of the features depicted and/or described therein, individually or relative to any other feature. Rather, alternative configurations can also provide substantially similar functionality as described herein, and are included within the scope and embodiments of the invention, whether expressly set forth herein or not. Numerous variations conceived according to such alternate embodiments are described below, and as informed by this description, other embodiments will become apparent to those having skill in the art.

Figure 2:
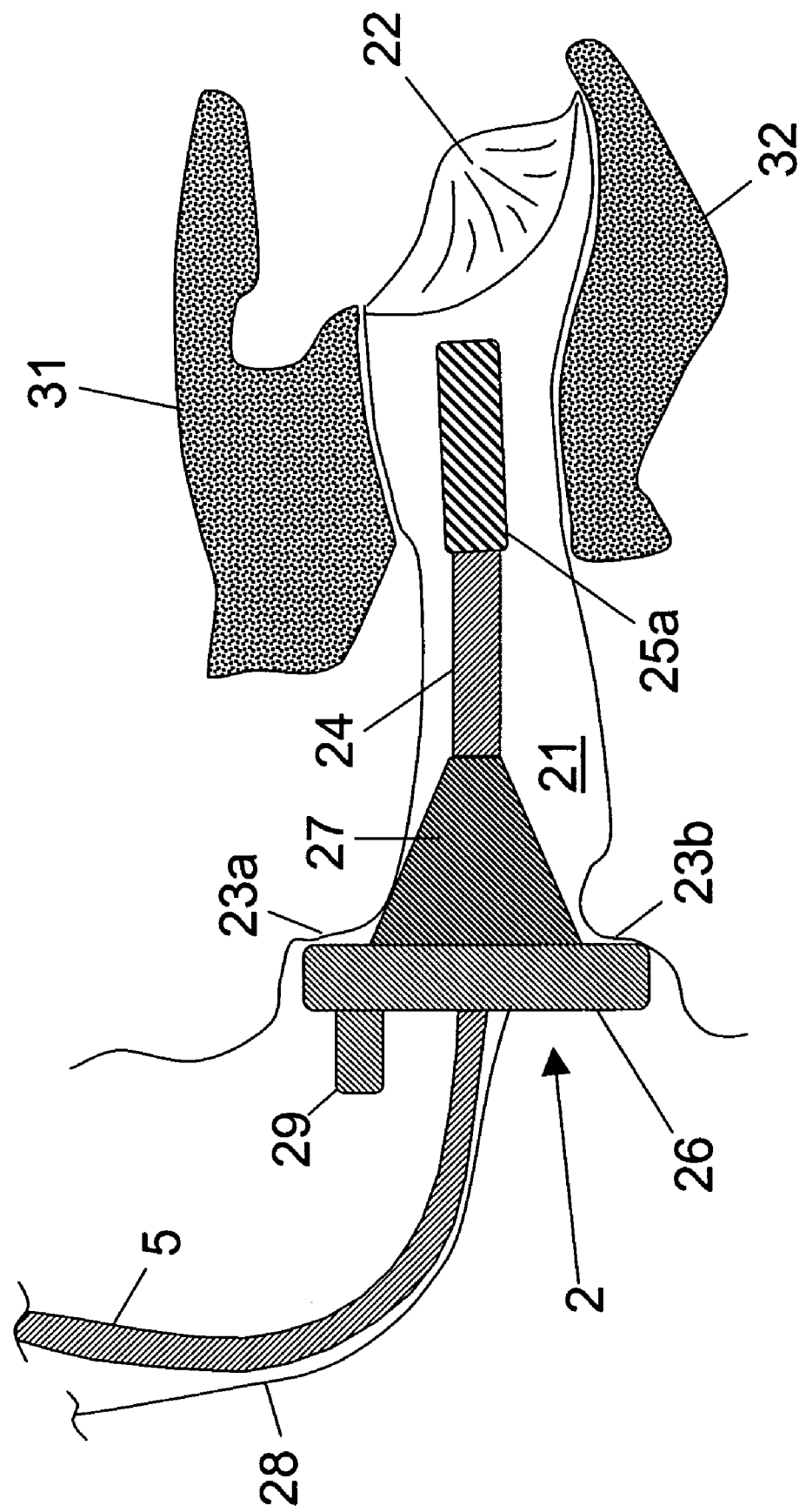
FIG. 2 depicts a portion of an airway obstruction correction apparatus positioned within a human auditory canal (canal shown in cross-section) and having a bladder not expanded with a fluid according to an embodiment of the invention.

FIG. 2 depicts an embodiment of an ear portion 2 of the apparatus positioned at least partially within an external auditory canal 21 (auditory canal) of a user. The ear portion generally includes a shaft 24 which extends into the auditory canal 21, but when properly positioned, does not contact and therefore avoids causing damage to the tympanic membrane 22. The shaft 24 may be either relatively flexible, allowing to conform somewhat with a curved auditory canal 21, or it may be relatively rigid, retaining a substantially constant shape during insertion, withdrawal, and regular use.

Figure 3:
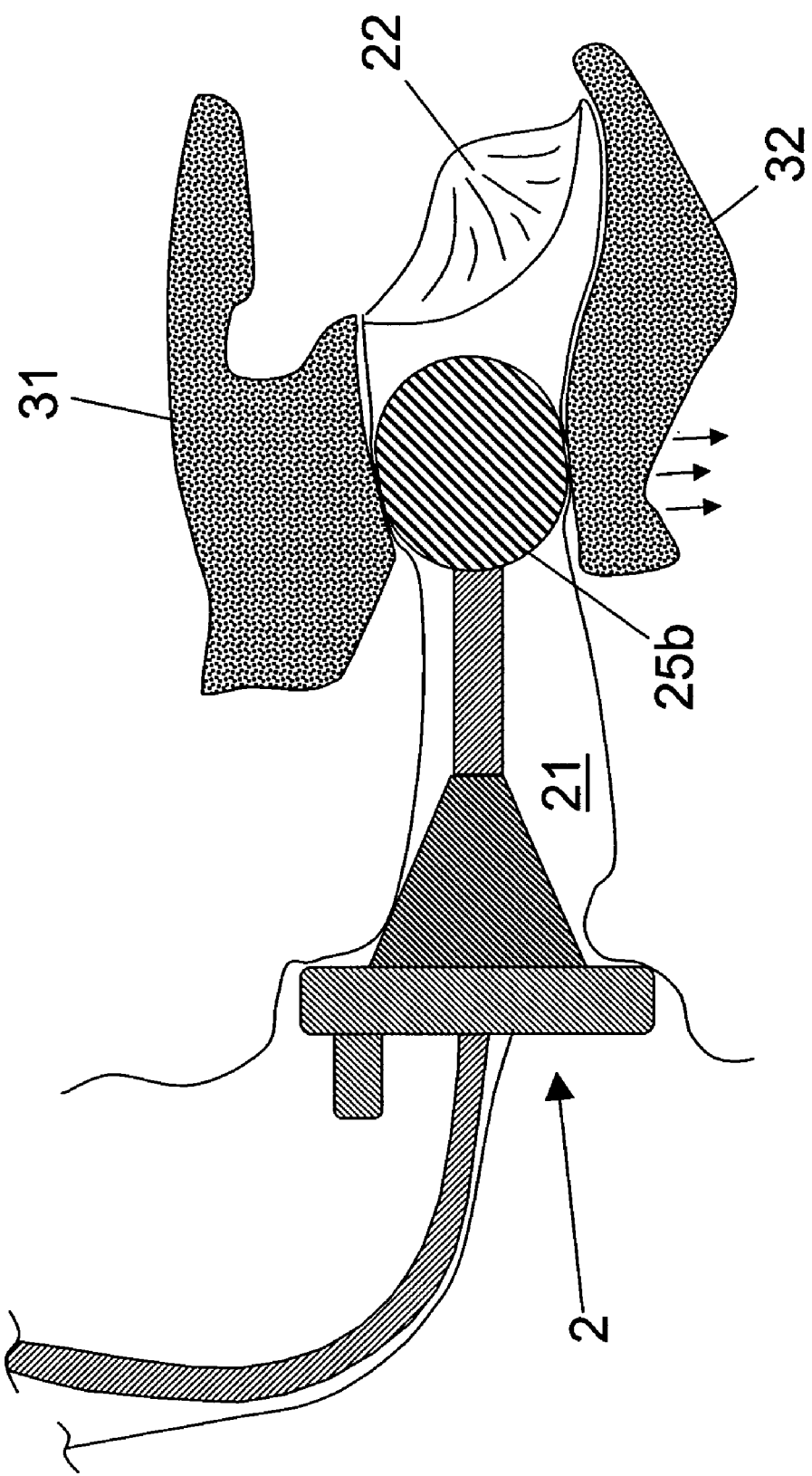
FIG. 3 depicts a portion of an airway obstruction correction apparatus positioned within a human auditory canal (canal shown in cross-section) and having a bladder expanded with a fluid according to an embodiment of the invention.
Figure 4:
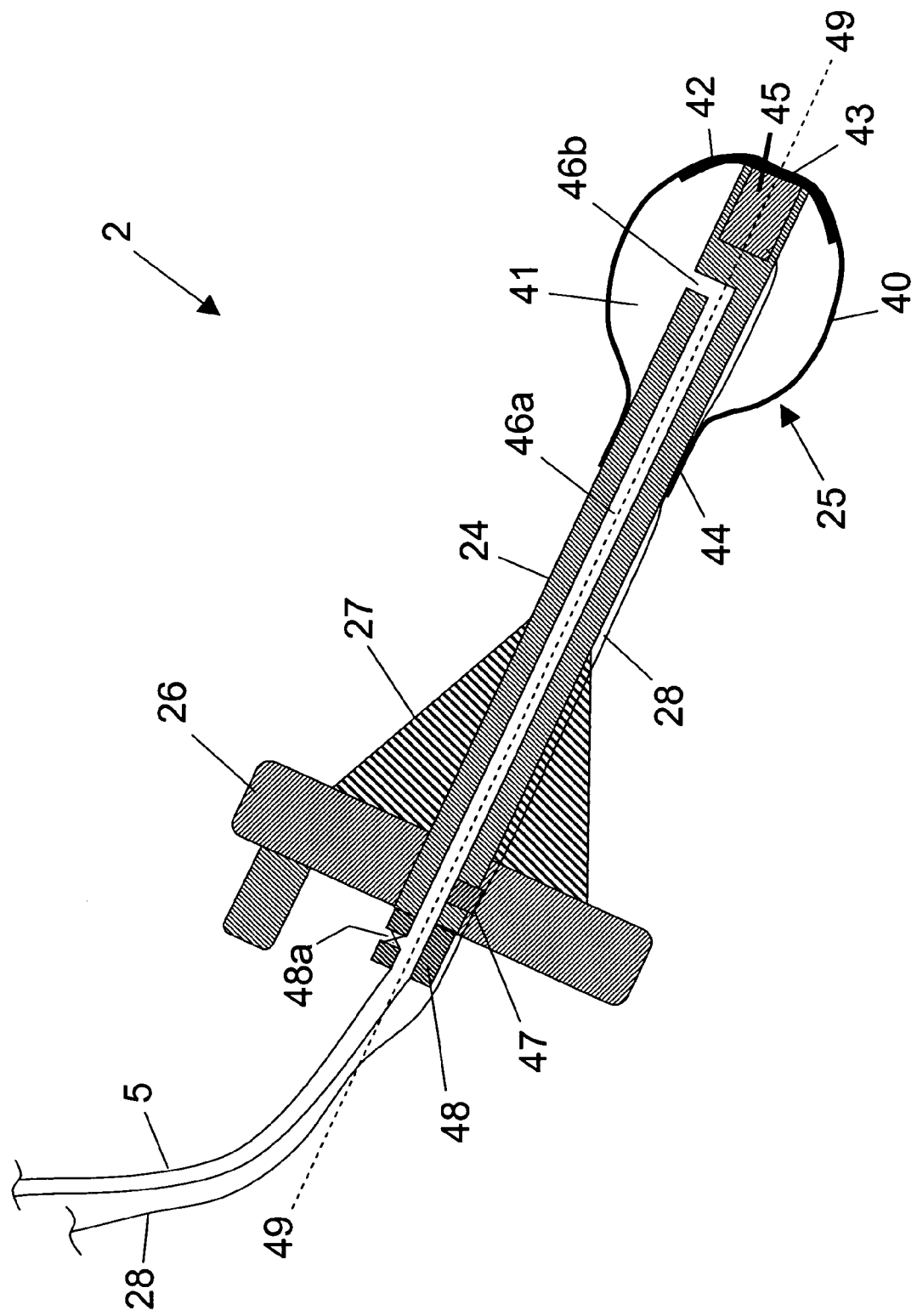
FIG. 4 depicts a cross-sectional view of a portion of an airway obstruction correction apparatus configured for insertion into a user's external auditory canal according to an embodiment of the invention.

A bladder 25 (as shown in FIG. 4) is operatively coupled proximate to the proximal end (relative to a medial line of a human user's body) of the shaft 24. A bladder 25 is typically either unexpanded as shown in FIG. 2 at 25a, or expanded as shown in FIG. 3 at 25b. The unexpanded bladder 25a normally remains relatively circumferentially conformal with the shaft 24, facilitating safe and relatively simple insertion of the shaft 24 and bladder 25a into the auditory canal. The shaft 24 generally possesses a longitudinal axis (at 49 of FIG. 4) radially centralized within the shaft and passing from an distal portion of the auditory canal 21 toward the tympanic membrane 22 when inserted into the auditory canal 21. The bladder 25a typically but not exclusively encompasses and encloses the proximal end of the shaft 24 (as shown in detail in FIG. 4), and is positioned approximately coaxially relative to the shaft 24. Therefore, the unexpanded bladder 25a can also be said to have a longitudinal axis which is the same as and/or substantially parallel with that of the shaft 24.

The bladder 25a is generally composed of an elastic material, and is configured to enable lateral volume expansion and contraction. The bladder includes opposing interior surfaces (proximate the shaft 24) and exterior surfaces (proximate the surfaces of the auditory canal 21 when in use). When a fluid pressure upon the interior surfaces within the bladder 25a exceeds an expansion threshold, the bladder 25a will expand as shown at 25b in FIG. 3, increasing the exterior circumference of the bladder 25a about (i.e., generally within approximately 45 degrees of perpendicular to) the longitudinal axis 49 of the shaft.

Coupled with the shaft 24 at its distal end is an insertion-limiting structure 26. The primary (although not exclusive) purpose of this structure is to limit the distance into the auditory canal 21 that the ear portion 2 can be inserted, because excessive insertion depth could cause the ear portion to contact the tympanic membrane 22, which could easily cause injury and perhaps impair the auditory function of the user. However, the insertion-limiting structure 26 also functions to facilitate sufficient insertion depth, and therefore appropriate positioning of the unexpanded bladder 25a relative to the jaw bones 32 (e.g., the condylar processes of the mandible) and other cranial bones 31 (e.g., the temporal bones or mastoid processes). The insertion-limiting structure 26 is typically greater in at least one dimension than the width of the nominal opening to the external auditory canal 21. Therefore, when inserting the ear portion 2 into the auditory canal 21, the insertion-limiting structure 26 contacts one or more portions of the outer ear structure, such as those shown at 23a and/or 23b, preventing further inward travel of the ear portion 2 into the auditory canal 21.

The insertion-limiting structure 26 will also generally be configured to prevent deformation thereof, which would otherwise enable excessive insertion. For example, the structure 26 may be formed of a sufficiently rigid material that deformation is avoided, or if formed of a flexible material, the structure 26 can have a sufficient thickness to substantially resist deformation such as would allow excessive insertion of the ear portion 2. Further, the insertion-limiting structure 26 can include a projecting structure 29 that can be manually gripped by a user to enable easy and safe extraction of the ear portion 2 from the auditory canal 21.

Proximate to the insertion-limiting structure 26, and intermediate the limiting structure 26 and the bladder 25a, one or more positioning spacers 27 enables location of the shaft 24 of the ear portion 2 substantially centrally within the auditory canal 21 (approximately equidistant from the interior surfaces of the auditory canal 21 in at least a portion of the canal 21). The positioning spacer(s) 27 will typically be configured with an inclined proximal (leading) edge, as shown in FIG. 2, to provide a guiding and/or wedging action during insertion into an auditory canal 21, although the embodiments are not so limited. Such wedging action causes the shaft 24 to assume and maintain a substantially central position within the auditory canal 21. In other embodiments, a plurality of positioning spacers 27 arranged relatively symmetrically and circumferentially around the shaft and each individually occupying only a portion of the circumference, can provide similar benefits. Additionally, although a positioning spacer 27 may be comprised of a relatively rigid material in embodiments, a somewhat compliant material will more easily conform to variations in the shape of an auditory canal 21, and will generally be more comfortable to a user.

Passing into the shaft 24 of the ear portion 2, typically but not exclusively through the insertion-limiting structure 26, is at least one passage 5 through which a fluid can be supplied to and/or withdrawn from the bladder 25a. The passage 5 may be a flexible tube according to some embodiments, but is not so limited. For example, the passage 5 may alternatively be formed at least partially within the relatively rigid material of a retention structure 3 and/or a positionally-adjustable connecting member 4 (shown in FIG. 1). Although a single passage 5 into the shaft 24 and bladder 25a is typical, an embodiment can also include multiple passages 5. For example, one passage 5 provides for supplying a fluid, while another may provide for removing a fluid from a bladder 25, such as in the event of an overpressure condition or other malfunction, or for normal operation within the apparatus.

In embodiments, at least one signal conveying means 28 (hereinafter, wire) also passes into the ear portion 2 to convey electrical signals to and/or from the ear portion. The one or more wires 28 may also serve other functions and provide other benefits in alternative embodiments, as will be further described below with reference to FIG. 4 for example.

As shown at FIG. 3, when properly positioned, a substantial portion of the bladder 25b is positioned intermediate the bones 31/32 located proximate to and partially surrounding an inner portion of the auditory canal 21 proximate to the tympanic membrane 22. Therefore, when the properly positioned bladder 25b expands into contact with the interior surfaces of the auditory canal 21 corresponding with the bones 31/32, a pressure of a fluid upon the interior surfaces of the bladder 25 also applies a force upon the bones 31/32 and intermediate tissue. The stimulus generated by this applied force generally causes an involuntary response by a user, including but not limited to adjusting the position of the jaw in an effort to reduce the force applied by the bladder. The user may also change sleeping positions in response the stimulus, also achieving an airway clearing condition.

Due to the structure of the upper airway in a human, adjustment of the jaw position to relieve pressure within the auditory canal 21 generally affects the upper airway in several beneficial ways. For example, because relaxation of the muscles surrounding the upper airway during sleep is a major contributing cause of airway obstruction (and therefore snoring and sleep apnea), adjustment of jaw position activates a number of the relaxed muscles, therefore contributing to a reopening of the airway. Similarly, as anyone who has yawned and/or adjusted their jaw to relieve inner ear pressure due to a change of altitude (and therefore, atmospheric pressure) has experienced, repositioning the jaw also affects the position of the soft tissues in the adjacent throat and airway passages. Therefore, adjustment of jaw position also beneficially affects an obstructed airway by repositioning the obstructing soft tissues and at least temporarily providing a clear airway and facilitating the user's breathing.

FIG. 4 provides a detailed and cross-sectional depiction of an ear portion 2 according to an embodiment of the invention, the features of which will now be described more fully. It is understood that any reference herein to a proximal end or distal end of a shaft 24 refers to an orientation relative to a medial line of a user's body when the ear portion 2 is inserted into the user's auditory canal 21, substantially as depicted in FIGS. 2 and 3.

Bladder 25 is generally comprised of an elastic material configured as a sac-like membrane 40 encircling and/or enclosing a proximal end 43 of shaft 24. A portion of the bladder membrane 40 opposite the shaft proximal end 43 is securely affixed to or pinched at least partially between separable sections of the shaft 24, to effect a leak-proof interface 44 entirely around the circumference of the shaft. Therefore, the proximal end 43 of the shaft 24 and a portion of the length of the shaft 24 proximate to the proximal end 43 is fully and hermetically sealed within the bladder membrane 40 according to an embodiment.

The leak-proof interface 44 can be achieved by use of an adhesive, a compressive wrapping, a mechanical pinching of the bladder membrane 40 circumferentially by a portion of shaft and/or a compressive or interlocking fastener coupled with the shaft 24, for example. Alternatively, the bladder membrane may in embodiments be heat sealed to the shaft to form a leak-proof interface 44. Of course, any combination of the listed sealing mechanisms and/or methods may be used, as well as any other which may be known in the art. Further, the mechanism and/or method used should produce a leak-proof interface 44 which remains so, without allowing fluid escape from the bladder 25 into the auditory canal 21, even under conditions of repeated expansion of the bladder 25, variable and/or sustained fluid pressure conditions, varying material and environmental temperatures and pressure (within a reasonably expected range), repeated insertion and extraction of the ear portion 2 from a user's auditory canal 21, and mechanical stresses due to handling and/or storage.

Between the leak-proof interface 44 of the membrane 40 with the shaft 24 and the proximal end 43 of the shaft 24, the membrane 40 remains separate from the shaft 24. Therefore, when a fluid is introduced in the bladder 25 and the membrane 40 expands in response to a fluid pressure within the bladder 25, a fluid filled chamber 41 forms within the expanding bladder 25b. The size and capacity of the chamber 41 is variable, depending upon such factors as the elasticity of the membrane 40, the size of the auditory canal 21, the volume and pressure of an introduced fluid, and other factors. When little or no fluid is present within the chamber 41, however, the unexpanded (i.e., contracted) bladder 25a is configured, as earlier described and shown in FIG. 2, to substantially conform with the shaft 24. Therefore, a transverse cross-sectional view of the ear portion 2 taken through the bladder 25 and shaft 24 would reveal that the radius of the unexpanded-bladder 25a generally exceeds the radius of the shaft by only approximately the thickness of the bladder membrane 40, according to a typical embodiment.

To prevent the bladder 25 from also expanding substantially along (i.e., within approximately 45 degrees from parallel to) its longitudinal axis and toward the tympanic membrane 22, the portion of the bladder membrane 40 directly proximate to the proximal end 43 of the shaft 24 is affixed with the proximal end 43 in embodiments. Therefore, expansion of the bladder 25 is substantially confined to and concentrated at the portions of the membrane 40 intermediate the leak-proof interface 44 and the proximal end 43, providing for expansion primarily about but not along the longitudinal axis 49 of the shaft 24. Additionally, in embodiments, a portion 42 of the membrane 40 positioned at and proximate to the proximal end 43 of the shaft 24 may be substantially thickened relative to portions of the bladder membrane 40 not so positioned. The thickened membrane portions 42 provide greater resistance to expansion as compared to the membrane 40 portions which are not thickened. This feature also substantially confines and concentrates substantial bladder expansion about rather than along the longitudinal axis 49 of the shaft 24.

Alternatively, the bladder may be configured with a donut-like shape, with the proximal end 43 of the shaft 24 passing at least partially through the center of the donut-shaped bladder. Therefore, the bladder mainly increases in diameter about the longitudinal axis 49 of the shaft 24, although the bladder itself does not have an apparent longitudinal axis. In such an embodiment, the bladder generally does not enclose the proximal end 43 of the shaft 24, unlike the embodiment depicted in FIG. 4. The shaft 24 may also be shortened, relative to that depicted in FIG. 4, to properly position the donut-shaped bladder.

Passing within and substantially parallel with the longitudinal axis 49 of the shaft 24 is a central duct 46a configured to convey a fluid between passage 5 and the interior chamber 41 of the bladder 25. In embodiments, as earlier described, central duct 46a may at least partially include a portion of passage 5 at least partially into the duct. The central duct 46a is therefore in fluid communication with both the bladder interior chamber 41 and the passage 5. The diameter of the central duct 46a can vary in different portions of the shaft 24, or can remain constant throughout, and the interior surfaces of the central duct 46a will generally be relatively smooth to avoid substantial turbulence in a flowing fluid. The central duct 46a will generally not, however, extend fully to the proximal end 43 of the shaft 24. Rather, the central duct 46a is generally in fluid communication with the chamber 41 of the bladder 25 at a point proximate to but spaced from the proximal end 43. The central duct 46a may, in an embodiment, deviate at an angle from the longitudinal axis 49 of the shaft 24 at a location proximate to the proximal end 43 to emerge as an orifice presented at the surface of the shaft 24. Alternatively, and perhaps more commonly, as depicted in FIG. 4, at least one transverse duct 46b may intersect with the central duct 46a and emerge as at least one orifice presented at a surface of the shaft 24 within a generally central region of the interior chamber 41 of the bladder 25. Therefore, a fluid passing through the central duct 46a toward the proximal end 43 will normally flow into and at least partially expand the interior chamber 41 of bladder 25.

Figure 5:
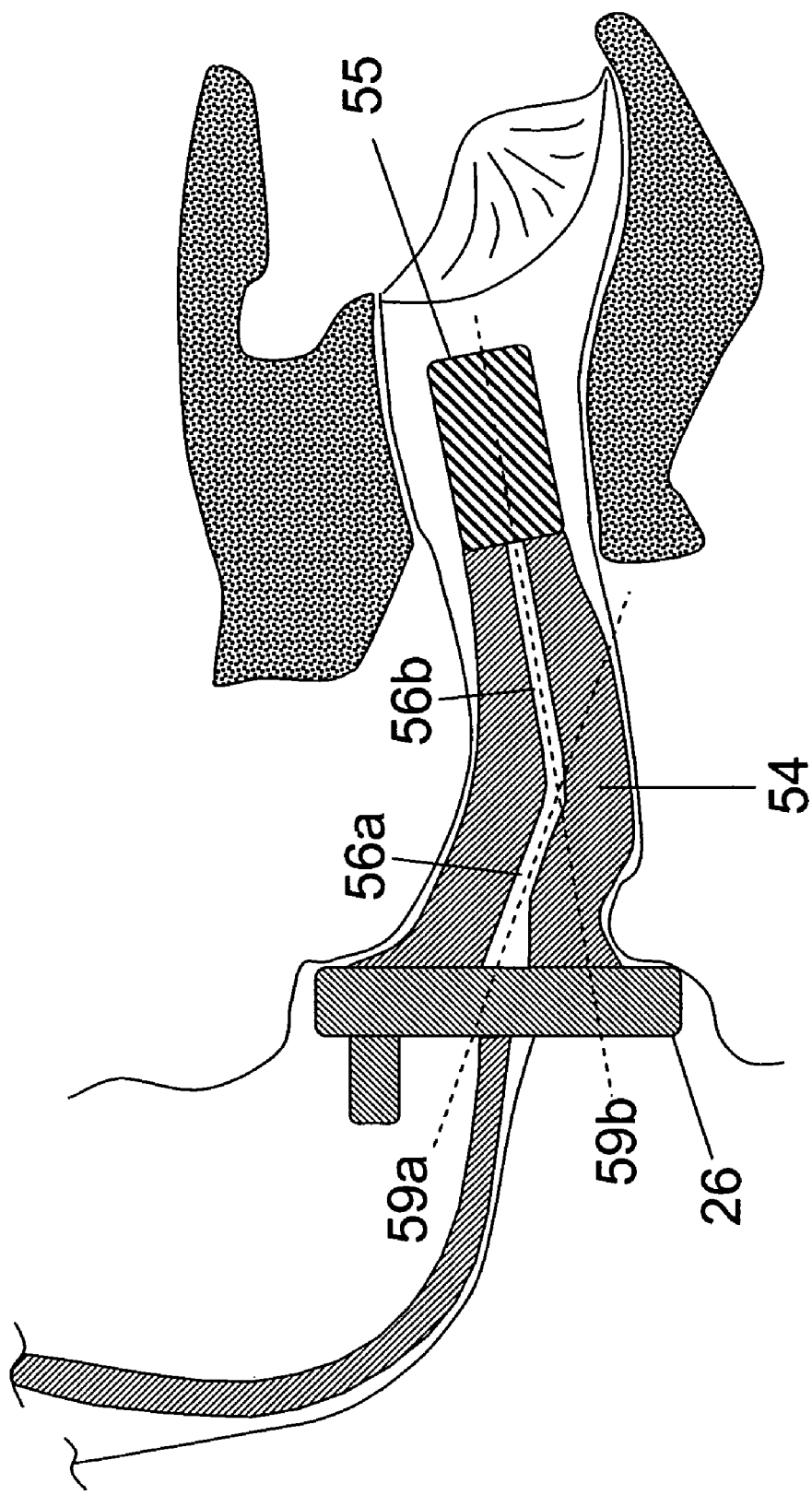
FIG. 5 depicts a portion of an airway obstruction correction apparatus positioned within a human auditory canal (canal shown in cross-section) and having a bladder not expanded with a fluid according to an alternative embodiment of the invention

Although the shaft is depicted in the figures as having a relatively straight overall configuration, cross-sectional configuration, and consistent diameter along substantially its entire length, beneficial embodiments can substantially vary from the depicted shaft 24. For example, a shaft can be configured to conform to the actual length and internal configuration of a user's external auditory canal 21, as depicted in FIG. 5. Therefore, the shaft 54 can vary in diameter, transverse cross-sectional configuration, and/or longitudinal angularity, providing a unique configuration for each auditory canal 21 of each user. In such unique configurations, a shaft 54 may not have a single longitudinal axis about which the shaft is substantially symmetrical. Therefore, in such embodiments, a longitudinal axis 49 as described herein may extend substantially parallel with a only portion of the central duct 56a, and be used as a relative reference point with regard to some other feature, structure, or direction. For example, shaft 54 has a first longitudinal axis 59a at a first portion of the central duct 56a proximate the insertion-limiting structure 26, and a second longitudinal axis 59b at a second portion of the central duct 56b proximate the bladder 55.

Further, when a shaft is substantially conformal with a user's auditory canal 21, as depicted by the shaft 54 in FIG. 5, it may not be necessary in all such embodiments to include a positioning spacer 27. Rather, the shape and overall configuration of the shaft 54 can sufficiently retain the ear portion 2 properly oriented and comfortably positioned within the auditory canal 21. In other words, the shaft can be configured to integrally incorporate such a positioning structure.

Referring again to FIG. 4, passage 5 is operatively coupled with the ear portion 2 and in fluid communication with central duct 46a. The internal diameter of passage 5 will generally correspond relatively closely with that of central duct 46a to avoid turbulence or pressure discontinuity, but the respective internal diameters need not match exactly. For example, as mentioned, at least a portion of passage 5 can extend at least partially into central duct 46a in embodiments. Therefore, in such situations, the internal diameter of the central duct 46a will correspond closely with the external diameter of passage 5.

As discussed, passage 5 is flexible in embodiments, and therefore the angle and/or orientation of passage 5 may deviate substantially from that of the longitudinal axis 49 of the central duct 46a even a short distance beyond the coupling point of the passage 5 with the ear portion 2. Although the central duct 46a is separately identified herein from the passage 5 for purposes of clarity, the central duct 46a and passage 5 can be collectively and broadly referred to and considered as a single contiguous passage for conveying fluid to and/or from the bladder 25. Therefore, reference herein to passage 5 indicates a specific structure, such as passage 5 in FIG. 4, whereas reference to a passage generally, without a numerical identifier, generally indicates the collective use of the term for a contiguous passage including the central duct 46a and passage 5 (as well as any or all fluid passages of an apparatus).

According to embodiments such as that depicted in FIG. 4, at least one pressure release mechanism 48 is operatively coupled in fluid communication with a passage. The pressure release mechanism 48 can be positioned nearly anywhere along passage 5, integrated with shaft 24 and/or bladder 25, or elsewhere as a part of the apparatus 1 in fluid communication with a pressurized fluid during operation. A beneficial purpose of a pressure relief mechanism is to relieve fluid and thereby reduce fluid pressure within the apparatus 1, and particularly within the bladder 25, such as during a malfunction condition of the apparatus. The pressure relief mechanism 48 may be electrically actuated to release fluid in response to a triggering event, for example an over-pressure condition sensed by a pressure transducer 47 and electrically communicated to the pressure relief mechanism 48. Alternatively, the pressure transducer 47 can be integral with or in mechanical communication with the pressure relief mechanism 48. In embodiments, the triggering event is the expiration of a preset duration of time (e.g., time limit) during which duration the fluid has remained pressurized (even if below an over-pressure threshold). Alternatively, the pressure relief mechanism 48 can release pressure by use of a pressure sensitive valve or similar structure placed across a duct 48a, the valve remaining closed below a preset pressure threshold, but opening to release fluid when the pressure threshold is attained and/or exceeded.

In an over-pressure situation, the release of fluid from the pressure relief mechanism 48 helps to prevent compressive and/or a dislocating injury to the tissues and/or structures lining or surrounding the auditory canal 21, and/or to prevent damage to the apparatus 1. For enhanced safety and device integrity protection, two or more pressure relief mechanisms can be used in an embodiment to provide an apparatus 1 with redundant pressure relief capabilities. Likewise, in embodiments having multiple pressure relief mechanisms 48, each may be located in a separate portion of the apparatus 1, enabling protective fluid release in a portion of the apparatus even though an over pressure condition does not exist in another portion of the apparatus. Therefore, although FIG. 4 depicts a single pressure relief mechanism 48, the embodiments are not so limited.

To enable release of fluid, a pressure release mechanism will typically include a duct 48a providing fluid communication between a fluid-filled passage and/or chamber of the apparatus 1 and an external surface of the apparatus 1. The duct 48a typically but not exclusively emerges as an externally presented orifice allowing fluid to be released outside the user's auditory canal 21. However, in embodiments, the fluid may be released through duct 48a into the user's auditory canal 21, or into some type of receptacle configured either as an integral component of the apparatus 1, or positioned separately from the apparatus to receive fluid released through the duct 48a by the pressure relief mechanism 48.

Located either within the duct 48a, or at either an entry or exit thereto, a valve or other similar structure normally obstructs the duct 48a to retain fluids within the apparatus 1. However, when a triggering event occurs, as described above, the valve or similar structure opens either partially or fully, creating a relatively unobstructed fluid pathway out of the apparatus 1 through the duct 48a. A valve generally provides for repeated use, by opening at the occurrence of a triggering event and/or condition, and closing again when the triggering event and/or condition ceases. As noted above, a valve can be a mechanical, integrated sensor/valve, or an electrically controlled valve. However, similar protective benefits can be obtained by from one-time-use mechanisms such as burst plugs, pressure sensitive membranes, or other such means. In such situations, an overpressure condition causes the structural integrity of the structure to fail, resulting in fracture, plastic deformation, or other substantially irreversible damage to the pressure release structure. In such cases, safe and proper function can generally be restored to the apparatus by replacing the structure, or replacing the entire pressure relief mechanism 48. In other situations, rather than the structural integrity of a valve mechanism failing, a retention force of a plug within the duct 48a is overpowered by the pressure of the fluid, causing the plug to dislodge from the duct 48a. Restoration of function may therefore simply entail replacing the plug within the duct 48a and replacing sufficient fluid to enable operative bladder 25 expansion.

FIG. 4 also depicts an electro-acoustic transducer 45 (hereinafter, microphone) located at the proximal end 43 of the shaft 24, although a microphone can be located elsewhere within or separately from the ear portion 2 according to alternative embodiments. When the airway of a sleeping user becomes at least partially obstructed, a microphone 45 detects audible indications of the presence of the obstruction. For example, when an airway is fully or substantially obstructed, a user generates audible indications (e.g., snoring, increased pitch of breathing sounds, etc.) of the obstruction by forcefully pushing air past the obstruction during breathing. However, even when the airway is less than fully obstructed, a restricted airway opening will frequently produce higher frequency indications (e.g., wheezing) of the tightening airway. These pre-snore sounds, when detected by a microphone 45 and interpreted as activation triggers for an apparatus, can enable a user to avoid the dangers associated with labored and/or interrupted breathing caused by a more fully obstructed airway. Alternatively, a microphone 45 can also detect the absence of normal breathing sounds, such as when breathing is interrupted in sleep apnea.

Pre-snore sounds can typically be very quiet, and occasionally even imperceptible to a nearby observer. However, a microphone 45 situated within a user's external auditory canal 21 proximate to the tympanic membrane 22 provides a unique capability to detect even very low amplitude sounds originating within the user's airway. Therefore, a microphone 45 can be advantageously located as in the embodiment depicted in FIG. 4.

A microphone so located must necessarily be relatively small in size, to fit unobtrusively within the auditory canal 21. Some particularly sophisticated (e.g., highly integrated and miniaturized) microphones may provide wireless transmission of signals including data corresponding to detected auditory indications of obstructed breathing. However, the more typical embodiment will include a wire 28 operatively coupled with the microphone 45, and continuing outwardly beyond the ear portion 2 of the apparatus. A wire 28 may lie alongside a shaft 24, as depicted in FIG. 4, or may lie at least partially within the shaft 24. Alternatively, the wire may continue only as far as the insertion-limiting structure 26, and therein or thereupon operatively couple with a wireless transmitter to transmit a signal including the detected auditory indications of obstructed breathing.

Although the microphone 45 in FIG. 4 is positioned advantageously near the proximal end 43 of the shaft 24, a microphone may be alternatively located externally from the auditory canal 21. For example, a microphone 45 could be positioned in contact with the throat of a user and held in place by a retaining mechanism (e.g., tape, adhesive, a band, a clip). A microphone 45 so positioned will generally detect even relatively quiet sounds emitted by a user, while also remaining fairly unobtrusive to the sleeping user. The location of a microphone 45 in embodiments is not limited by these examples, but it is understood both close proximity to the originating location of a sound, and sensitivity of the microphone 45 to sounds in the correct frequency range, provide advantages in early detection of snore and pre-snore sounds. Further, as indicated, the apparatus 1 and its various operative components should not be so located and/or configured as to interfere with a user's comfortable and relatively uninterrupted sleep.

As discussed above, the apparatus 1 can include a pressure transducer 47 (hereinafter, transducer) configured to detect a pressure condition of a fluid within the apparatus 1. An optimal location of the transducer 47 will enable relatively accurate measurement of fluid pressure within the bladder 25, which further allows a relatively accurate determination of the pressure exerted by the bladder 25 upon the surfaces of an auditory canal 21. Therefore, a transducer 47 may be optimally located near the proximal end 43 of the shaft 24 within the bladder 25. However, because a fluid pressure condition nearly anywhere within a passage between a bladder 25 and a pressurizing mechanism (e.g., pump) is typically approximately equivalent, the transducer 47 can be provided as depicted in FIG. 4 or in a wide variety of locations along a fluid passage between a bladder 25 and a pressurizing mechanism (e.g., pump). A portion of the transducer 47 will also typically be presented in contact with the fluid, or in contact with a flexible membrane or other structure which is in contact with the fluid. If separated from the fluid by a structure, the structure will generally be configured to deflect, temporarily deform, or otherwise respond proportionally to changes in fluid pressure in a manner which can be detected by the transducer 47. The transducer 47 then generates a signal in response to a fluid pressure condition which represents proportionally the fluid pressure condition.

A signal indicating a fluid pressure condition is conveyed from a transducer 47 to a data processing device (e.g., microcontroller) by a wire, which can be the same wire 28 as is also coupled with the microphone 45, or can be a separate wire, whether combined within a common bundle of wires or routed independently from another wire 28. For convenience and user comfort, to minimize tangling and/or damage to wires, and to provide other benefits, wires 28 are generally closely coupled with a fluid passage for at least a portion of the distance between the ear portion 2 and the control unit 7 or another destination device. As used herein, processing data can include nearly any activity performed by a device, system, entity, process, and/or software program, for example, upon or in response to data, including reading, storing, altering, analyzing, converting, conveying, responding, or otherwise changing at least one condition, status, or configuration of an apparatus 1 or any part thereof based at least in part upon such data.

As indicated, both a microphone 45 and a transducer 47 are capable of converting a non-electrical signal, sound and pressure respectively, into an electrical signal. In embodiments, a microphone 45 and/or a transducer 47 includes and/or is operatively coupled with a power source (e.g., locally or remotely located relative to the microphone 45 or transducer 47), is configured to induce power gain to an electrical signal, and therefore would constitute an 'active transducer'. However, each or both (or all) may alternatively be passive transducers, without the capability to induce power gain to an electrical signal.

Although not depicted in FIG. 4, embodiments of an ear portion 2 enable removal and replacement of individual components of the ear portion 2, and/or combinations of components. For example, in such embodiments, it is possible to remove and replace such components as the transducer(s) 47, the pressure relief mechanism(s) 48, the position spacer(s) 27, the microphone 45, or others. Likewise, although not shown, it may be possible to separate the proximal end 43 of the shaft 24 including the microphone 45 and/or bladder 25 from the remainder of the shaft 24 at a junction located between, for example, the leak-proof interface 44 and the insertion-limiting structure 26. The provided junction would be sufficiently securely coupled and sealed to prevent fluid leakage and/or other integrity failures during use, yet enable relatively simple removal and replacement by a user or other entity (e.g., a health care provider).

Therefore, in the event of excessive wear and/or failure of individual components, the components can be replaced without the need to replace the entire apparatus 1 or even the entire ear portion 2. Alternatively, the ear portion 2 may be provided as an integral unit, and failure of any component within the ear portion 2 can be remedied by detaching the ear portion 2 from a fluid passage 5 and/or a wire 28, and by coupling a fully functional replacement ear portion 2 thereto.

While FIG. 4 depicts numerous operative components and positional relationships between components, FIG. 4 represents only one embodiment of the invention and does not limit alternative configurations and/or combinations of components. FIG. 4 is not depicted to scale, and many variations are conceived to accommodate the unique configurations of users' auditory canals and/or individual abilities to tolerate a wearable apparatus while sleeping. Therefore, FIG. 4 is provided diagrammatically to provide understanding of an embodiment of the invention in light to the description provided herein.

While an end of each of a passage 5 and/or a wire 28 is operatively coupled with an ear portion 2 as shown collectively in FIGS. 1-4, an opposing end of each of the wire 28 and/or the passage 5 is operatively coupled with the control unit 7 in embodiments. The control unit 7 is worn by or otherwise affixed to a user (e.g., carried in a pocket of an apparel item, retained by an encircling strap on an arm or torso), or may be located separately from the user (e.g., on a bedside table or shelf, affixed to a bed, retained in a holder affixed to or placed on a surface). Each of the passage 5 and/or wire 28 may pass through an aperture in a housing 7a of the control unit 7 and extend into the interior of the housing 7a, or may couple with and terminate at a coupling 60 configured at and presented to an exterior surface of the housing 7a. Thereafter, a separate passage and/or wire extends within the housing 7a from the coupling to at least one internal component. In such embodiments, although separable one from the other at the coupling 60, a passage 5 external to the housing is in fluid communication with, and forms a substantially hermetic (e.g., leak-proof or leak-resistant) connection with the passage from the coupling 60 to an internal component.

Figure 6:
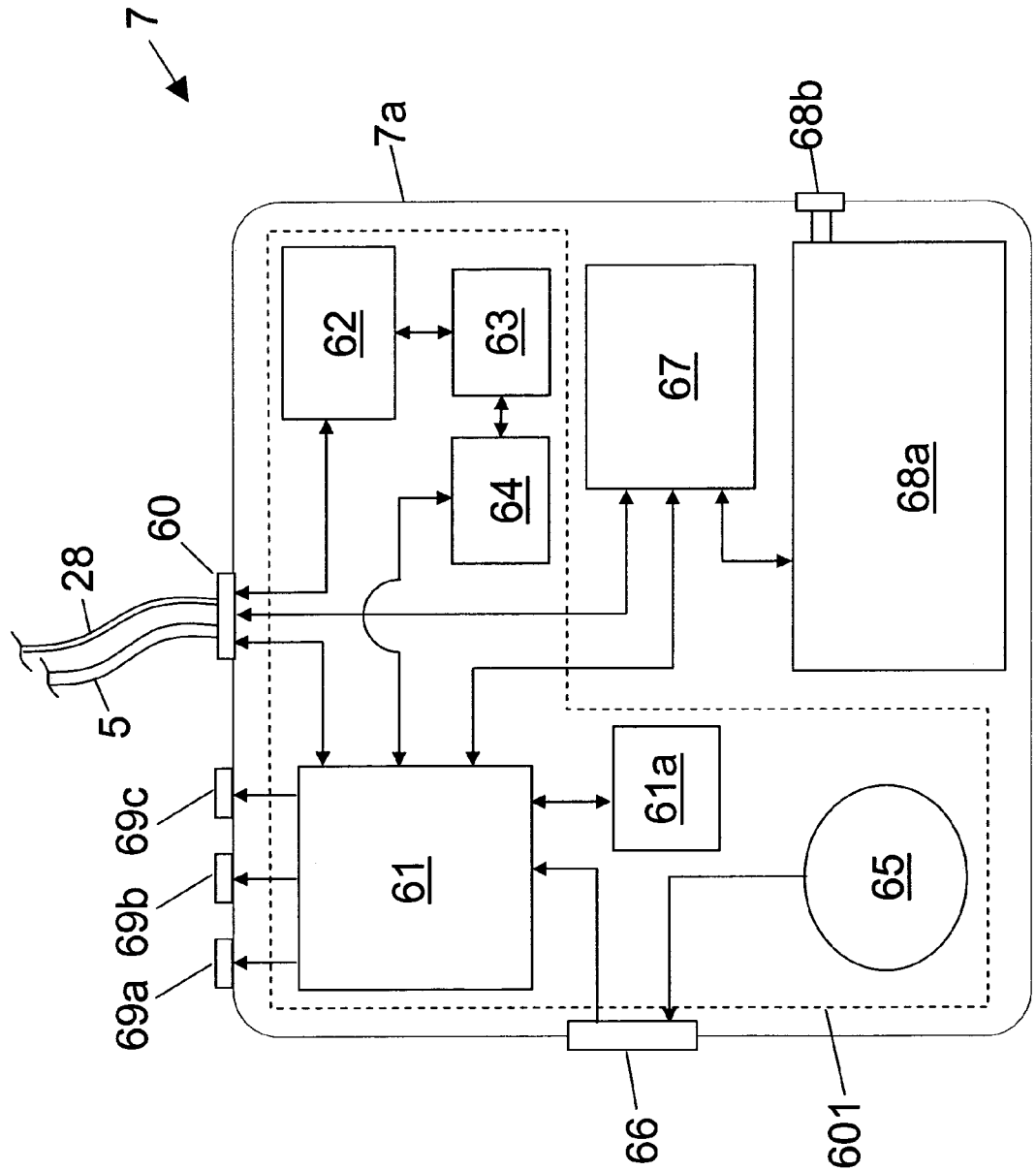
FIG. 6 depicts a block diagram of a control unit of an airway obstruction correction apparatus according to an embodiment of the invention.

Generally, a fluid passage is operatively coupled with a pump 67 contained within the housing 7a of a control unit 7, according to the embodiment depicted in FIG. 6. The pump 67 may be configured to induce flow in only one direction, from the control unit 7 toward the ear portion 2 for example. Alternatively, the pump 67 could additionally be configured to also induce flow from the ear portion 2 toward the control unit 7, enabling expansion and contraction of the bladder 25 by altering the operation of the pump 67. The pump 67 derives power from a power source, such as a battery 65. The battery 65 can be either replaceable or rechargeable, and can assume any of numerous configurations according to the size, voltage, or other operational parameters of selected components of an apparatus 1. For example, FIG. 6 depicts a coin cell battery 67, such as a lithium ion, long life battery. Use of a battery enables great flexibility in placement of a housing during use, due to the lack of need for a power cable connected to a wall-mounted electrical power outlet, for example. Alternatively, however, power can be derived via a power cable coupled with a wall outlet in embodiments.

The quantity of fluid needed to expand one or more bladders 25 is fairly limited. Therefore a pump 67 can likewise be fairly small, and in particularly beneficial embodiments, the pump 67 will produce very little noise when operating. Therefore, repeated operation of the pump 67 is unlikely to substantially interfere with a user's uninterrupted sleep. For example, a piezoelectric pump is used according to an embodiment. Further, a pump 67 will typically transfer a sufficient volume of fluid per unit time to provide for relatively quick expansion of a bladder 25, while also delivering fluid in sufficiently small increments to enable substantial control over the extent of bladder 25 expansion. For example, it may be preferable to expand a bladder sufficiently to cause a user response within 5-15 seconds, however shorter and/or longer expansion times are also acceptable according to other embodiments. Sufficient control of bladder 25 expansion can include controlling an expansion condition (e.g. expansion, contraction) of a bladder 25 after detection of an expansion end point condition (e.g., achieving a pre-set fluid pressure target) within ±2-5%. A preferred embodiment will achieve a deviation from an expansion end point condition of less than 2%, while in other embodiments, deviations of 5-10% or even higher may also be tolerated while producing beneficial results.

A pump 67 is typically also operatively coupled in fluid communication with a fluid reservoir 68a from which fluid can be withdrawn by an action of the pump 67 to expand the bladder(s). The reservoir 68a can retain all or a majority of the fluid in the apparatus 1 when the bladder(s) 25 is/are not in an expanded condition. The reservoir 68a can be a relatively rigid structure, retaining a consistent shape and fluid capacity, or can be collapsible, changing shape and/or fluid volume in response to the withdrawal from and/or replacement of fluid into the reservoir 68a. For example, the reservoir 68a can be a compressible sac-like enclosure which is compressed by a gas pumped into a space surrounding the sac within a second, more rigid enclosure. In such an embodiment, fluid passages 5 carrying a fluid to the ear portion 2 will operatively couple with the reservoir 68a rather than with the pump 67. In other embodiments, a pump 67 and a reservoir may be integrated as, for example, a cylinder and plunger design. Activation of the pump causes a plunger (e.g., piston) to progress through a fluid-filled cylinder, reducing the capacity of the cylinder and forcing the fluid to exit the cylinder via a fluid passage 5. One of ordinary skill in the art will recognize that a great number of embodiments lie within the scope of the invention according to alternative embodiments.

Because the fluid volume in an apparatus 1 can vary substantially depending upon the diameter, length, and number of passages, the size, configuration and number of bladders 25, and other factors, the fluid capacity of a reservoir is highly variable between alternative embodiments. Fluid capacities in the range of 5-60 milliliters are expected in embodiments, although this range is not exclusive and larger or smaller capacities in embodiments will not depart from the scope or spirit of the invention.

The reservoir 68a is also, in embodiments, provided with a port 68b for adding, replenishing, withdrawing a fluid or otherwise adjusting the volume of fluid in the reservoir. The port 68b generally can be easily opened and closed to enable fluid transfer, and is relatively hermetically sealed (e.g., leak-proof or leak-resistant) during normal operation.

Activation of a pump 67 is controlled by a microcontroller 61, typically but not exclusively also provided within the housing 7a of the control unit 7. The microcontroller 61 is also operatively coupled with a power source such as battery 65, although an activation control 66 (e.g., switch) is typically interposed between the battery 65 or other power source and the microcontroller 61. The activation control 66 is generally presented to the exterior of the housing 7a and accessible to a user. Alternatively, an activation control can be partially and/or entirely retained within a housing 7a and can provide for activation by use of a wireless remote control means (e.g., infrared, radio-frequency) or a wired means (e.g., USB cable, optical fiber). Therefore, an activation condition of the microcontroller 61 and other components of the apparatus 1 can be directly and/or remotely controlled by a user or another entity (e.g., a health care profession, an automated monitoring and control device system or device).

Referring to FIG. 6, the components and/or function of a control unit 7 may be most simply and clearly described according to an operational flow of the apparatus 1, as follows. A microphone 45 detects an auditory indication of an obstructed airway, and sends a signal via wire 5 to the control unit 7. The wire 5 is operatively coupled with an amplifier 62 configured to augment the received signal. The augmented signal is conveyed from the amplifier 62 to a analog-to-digital converter 63 configured to convert the received analog signal into digital form for analysis by the microcontroller. The signal then can be conveyed to a tunable audio filter 64, which is configured to discriminate between a signal including data closely corresponding to the sound frequencies of a user's normal breathing, and a signal including data diverging from that of the user's normal breathing. Each user's breathing airways can produce relatively individualized frequencies, pitch, or changes in pitch based at least partly upon upper airway structure. For this reason, a tunable audio filter 64 enables customization of an apparatus 1 to the individualized sound characteristics of each user's airway, and allows the setting of corresponding individualized activation (snore trigger) thresholds. A tunable audio filter 64 can be preset by a health care provider, or as discussed below, can likewise be adjusted remotely.

Alternatively, rather than a tunable audio filter 64, a signal can be conveyed from a converter 63 to a digital low pass filter to filter out data in the signal corresponding to high frequency sounds, and a threshold detector then identifies if a threshold for activation is detected in the remaining sound data of the signal. Any or all of the amplifier 62, signal converter 63, and tunable audio filter 64 (or digital low pass filter and threshold detector) (collectively, audio components) can be integrated into the microcontroller 61 according to alternative embodiments.

When a snore trigger is detected based upon sound characteristics represented by data in a received signal, the microcontroller 61 will send an activation signal to the pump 67 causing the pump 67 to activate and begin transferring fluid from the reservoir, 68a to the bladder(s) 25 via the fluid passages 5. An activation signal will typically, but not exclusively, initially be configured to cause a pump 67 to transfer a relatively small amount of fluid. Thereafter, characteristics of the activation signal will typically be progressively modified by the microcontroller 61 to cause a gradually increasing rate of fluid transfer from the pump 67 until a peak transfer rate is attained. This produces a slowly increasing pressure within a user's auditory canal 21 and helps to avoid rousing the user from their present level of sleep. Therefore, it should be understood that a pump 67 is, in embodiments, configured to be capable of variable fluid transfer rates in response to variable characteristics (e.g., frequency, amplitude, waveform, etc.) of an activation signal.

As the bladder(s) 25 expands, the increased volume of fluid conveyed into the bladder(s) 25 and fluid passages, interacting with the resistive, compressive force exerted by the elastic bladder membrane(s) 40, cause the fluid pressure to increase within the fluid passages and bladder(s) 25. The pressure transducer 47 monitors the fluid pressure, and sends a signal to the microcontroller. If the fluid pressure rises to or above a threshold level preset and retained in a memory device 61*a* within and/or operatively coupled with the microcontroller 61, the microcontroller 61 will alter or terminate the activation signal to the pump 67, causing the pump 67 to decrease a rate of or cease altogether the pumping of a fluid.

Alternatively, the pump 67 continues to pump fluid toward and into the bladder(s) 25 until a preset duration of time expires, at which point the microcontroller 61 terminates the pump activation signal, causing the pump 67 to cease pumping a fluid. In yet another situation, the pump 67 will continue to transfer fluid toward and into the bladders 25 until the microphone 45 detects, and the audio components in the control unit 7 confirm the absence of sounds consistent with an obstructed airway. Upon such confirmation, the microcontroller 61 will terminate the pump activation signal, causing the pump 67 to cease pumping fluid. In embodiments, cessation of pumping allows the elastic membrane(s) 40 of the bladder(s) to contract, forcing fluid back through the fluid passages and into the reservoir 68*a*. In other embodiments, rather than terminating a pump activation signal, the microcontroller may send a signal causing the pump to return fluid from the fluid passages and bladder(s) 25 to the reservoir 68*a*, causing the bladder(s) 25 to contract.

Once an operative fluid pressure (e.g., sufficient to normally induce an airway adjusting user response without causing injury to an auditory canal 21) is attained within the bladder(s) 25, such pressure can be maintained either by a microcontroller 61 controlled pumping pace sufficient to counteract any fluid backflow through the system, or by a microcontroller 61 controlled closure of a backflow prevention valve in fluid passages between the pump 68 and the bladder(s) 25. An operative pressure may be found in the range between approximately 5-300 millimeters of mercury (mmHg), although in many situations, a fluid pressure in the range of approximately 20-80 mmHg is sufficient to induce an airway adjusting user response. Typically, a maximum effective fluid pressure below 40 mm may be maintained and present little danger of injury to a user. Once an operative (e.g. preset target) fluid pressure level is obtained, it is thereafter maintained for a preset duration of time, or until detecting the absence of indications of an obstructed airway obstruction, until a system malfunction is detected, or until the apparatus 1 is deactivated by the user or another, as determined according to preset configuration parameters.

Functionally, it is a pressure exerted by an expanding bladder 25 upon the bones and intervening tissues surrounding an auditory canal 21 that induces an airway adjusting user response. However, in most cases, it is easier and more practical to monitor and control fluid pressure in the apparatus 1 than to measure the actual pressure exerted by a bladder 25 upon an inner surface of an auditory canal 21. Therefore, the relationship between various fluid pressure ranges and user responses can be tested by a health care professional, and corresponding fluid pressure thresholds and pressurization time duration limits can be preset and stored in a memory device 61*a* of the apparatus 1. Alternatively, a healthcare provider can remotely monitor the function of an apparatus 1 and the corresponding responses of a user during normal use via an extended system enabling transfer of data between the user location and the healthcare provider location. This system is described in further detail below.

As further shown in FIG. 6, various status indicators 69*a-c* can be provided at or within (and visible through) the housing 7*a* of the control unit 7, enabling a user to monitor operational conditions of the apparatus 1. Status indicators 69*a-c* may most typically be light emitting diodes (LED), but are not so limited. For example, an indicator 69*a* can be provided to indicate a power actuation status of the apparatus 1. When the apparatus power switch 66 is first turned, the microcontroller 61 will execute a test algorithm, to ensure the apparatus 1 is prepared for normal operation. The algorithm can include inflating and deflating the bladder, as well as testing continuity and function of at least a subset of the electronic components. Either during execution of the algorithm, or following successful completion thereof, the power actuation indicating can flash to provide a visual indication to the user. Another indicator 69*b* can indicate a power level condition of a battery 65. The battery power level indicator can flash or change color, for example, to indicate when the power level of a battery falls below a preset threshold, enabling a user to avoid untimely apparatus failure by either deactivate the apparatus or by replacing, recharging, or otherwise restoring an adequate power source condition. A third indicator 69*c* can indicate an inadequate fluid level in the apparatus 1, a pressure condition of the fluid, an apparatus memory failure, or some other condition that can potentially affect proper apparatus 1 function. More or fewer indicators may be provided in other embodiments than are described herein.

Components such as but not limited to the microcontroller 61, memory device 61*a*, and analog-to-digital converter 63 can be implemented as solid state devices (e.g., packaged integrated circuit devices), contributing to a relatively small control unit 7 yet providing relatively sophisticated data processing capabilities. A control unit 7 will also, in embodiments, include a printed circuit board 601 or another substrate with which one or more of the components are either durably (e.g., soldered) and/or removably (e.g., socketed) coupled.

Airway Obstruction Correction System

Thusfar, embodiments of an apparatus for correcting an obstructed airway condition have been described. However, as depicted in the embodiment shown in FIG. 7, the invention described herein also includes embodiments of a system including the described apparatus. A system can include elements and/or components which are all located locally relative to the user, but can also include remotely located elements and/or components in an extended system 70. An example of a local system could include the apparatus 1 and computing device 73 (e.g., personal data assistant, desktop or mobile computer) or other electronic appliance (individually and/or collectively hereinafter, computer) configured to received data-bearing signals from the apparatus 1. A local system can further include more than one apparatus 1, for example when a plurality of users are located within a relatively limited area (e.g., within a single house, facility or compound), and/or more than one computer 73.

Typically, a computer 73 will include a data storage means (e.g., magnetic hard disk drive and/or media, memory chip and/or module, operatively coupled peripheral data storage device, optical storage device and/or media, magnetic tape drive and/or media) configured to enable storage and/or retrieval of the received data-bearing signals. The computer 73 can be operatively coupled with the apparatus 1 by a tangible, wired connection, or wirelessly. Because a user may move about while sleeping, a wireless connection provides benefits by avoiding tangling of a wire, and/or problems with a connected wire being too short to allow free movement by the user. Therefore, in wireless embodiments, an apparatus will also included a wireless signal receiver, generally but not exclusively included at least partially within the control unit housing 7*a*.

Likewise, embodiments of an apparatus 1 can also include a wireless transmitter configured to transmit data from the apparatus to a local and/or remote data processing device 73/71. Either or both of the transmitter and receiver of an apparatus 1 can be at least partially integrated with the microcontroller 61, or can be at least partially separate components operatively coupled with at least one of the microcontroller 61 and/or the microphone 45. Of course, in wired embodiments of an apparatus, one or both of the receiver and/or transmitter are configured for data transfer by wire rather than wirelessly.

The computer 73 can also be configured to enable analysis of the received and/or stored data, and display of the data and/or analysis results to a user or other entity. Analysis capabilities can be embodied at least in part as software stored on or accessible by the computer 73. The analysis capabilities can, for example, create and display at a display means, to a user or other entity, a visual representation (e.g., graph, table) of the data, and/or automatically alter configuration parameters of the apparatus in response to detecting the presence in the data of certain preset alteration triggers. Configuration parameters can include any setting, parameter, threshold, data, or other variable input which affects the performance, capabilities, responses and/or output of an apparatus. A preset configuration parameter is one which is determined and/or activated for application at any time prior to its operating on or in response to a condition, threshold, or circumstance for which it is intended to operate, or for which it may operate although not so intended. As such, the limitation of being "preset" is merely a temporal limitation according to a typical embodiment.

The computer 73 will, in embodiments, also include a display means (e.g., monitor, printer) for visually displaying data to a user, and/or a data input means (e.g., mouse, keyboard, microphone, touch-sensitive screen), as well as other potential peripheral devices (e.g., printer, modem, router, scanner, camera). A data input means allows a user or another to input data manually, and/or to input configuration parameters that can be conveyed to the apparatus 1 to alter at least one configuration parameter of the apparatus. For example, when the duration of bladder 25 expansion is a configuration parameter of the apparatus, a different duration can be input at the computer 73 and be transmitted to the apparatus. After receiving the transmitted configuration parameter, an existing duration configuration parameter stored within a memory means 61a of the apparatus 1 is replaced by the transmitted duration configuration parameter. This is but one example, and numerous other configuration parameters enabling and/or affecting data acquisition and/or transmission, or safe and effective operation of the apparatus 1 by the user, may be similarly affected.

Figure 7:
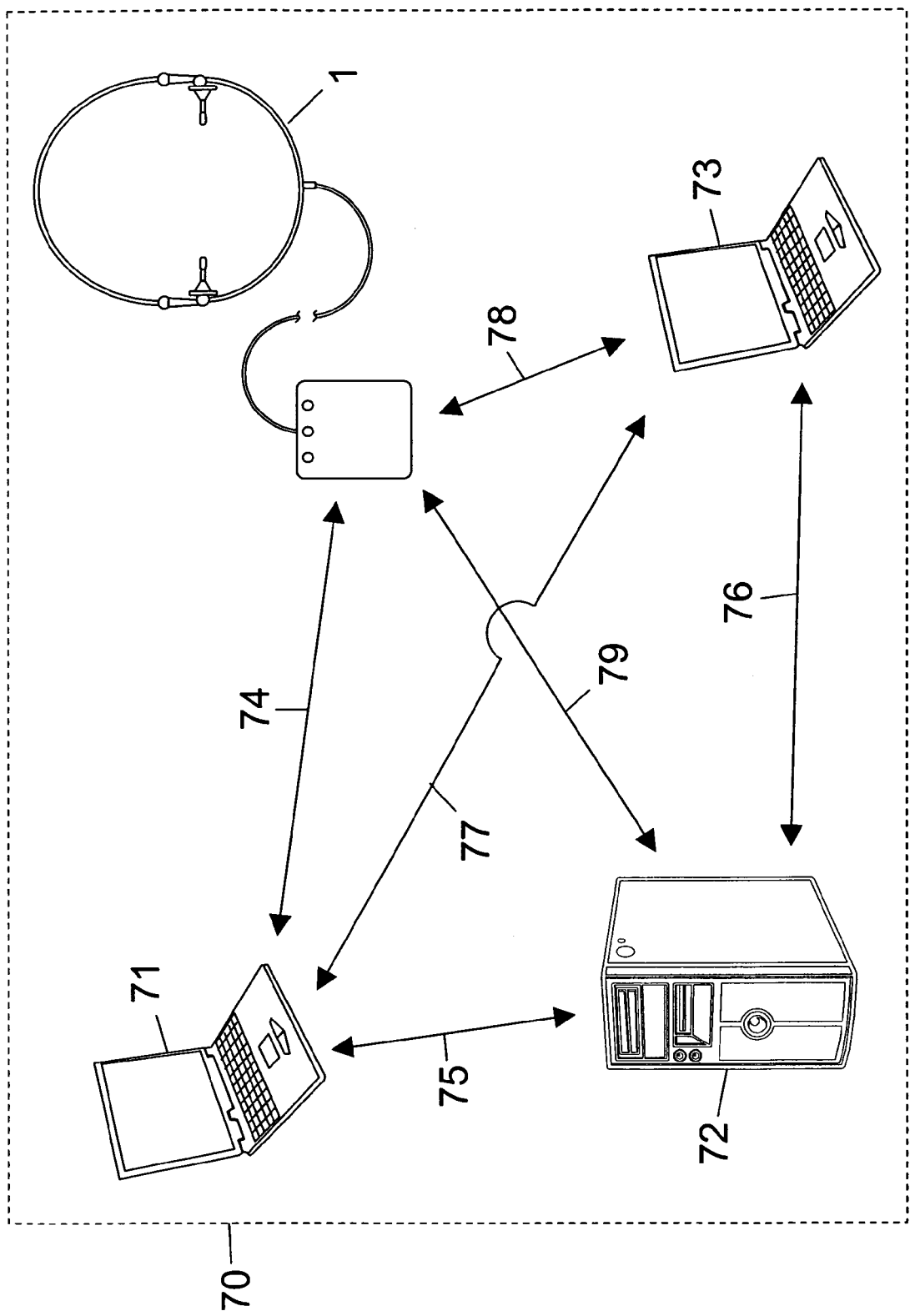
FIG. 7 depicts an airway obstruction correction system according to an embodiment of the invention.

As described herein, and as depicted in FIG. 7, a data pathway 78 typically exists in a system 70 between an apparatus 1 and a computer 73, such pathway 78 being either unidirectional or bidirectional, and either wired or wireless according to alternative embodiments.

An extended system 70 can include one or more remotely located devices 71 of the same and/or similar nature and/or capabilities as local computer 73, or alternatively, remote device 71 can include additional capabilities with which the local computer 73 is not configured. A single remote computer 71 may also comprise a portion of more than one extended system 70, such as when the remote computer 71 is linked by networking means with more than one apparatus 1 and/or local system. A remote computer 71 can include capabilities to transfer data-bearing signals directly with an apparatus 1 and/or with a local computer 73. Alternatively, the remote computer 71 can relay data-bearing signals to the apparatus 1 and/or local computer 73 through a network signal conveying device 72 such as a server and/or other device or service. Server 72 can be an internet server, for example located at or controlled by an internet service provider or other internet linked entity. The server can also be located locally relative to either of the local computer 73 or the remote computer 71. Alternatively, rather than a server, the signal relaying device 72 can be a router, modem, phone system interchange device, satellite, wireless signal transmission tower, or other signal conveying structure, device, or service.

Data-bearing signal pathways 74-77 and 79, like pathway 78, can be either wired or wireless. Further, as depicted by pathways 74-79, data-bearing signals can be conveyed either directly or indirectly between any device (e.g., computer, apparatus, server) any other device in a network, according to alternative embodiments of the invention. Signals can be conveyed by, for example, terrestrial telephone systems, mobile phone systems, broadband cable communication systems, satellite communication systems, wireless computer protocols and systems (e.g., WiMAX, WiFi, WAN, LAN), radio and/or microwave-based communication networks, or others currently in user and/or conceived for transferring data-bearing signals. Likewise, each of signal pathways 74-77 and/or 79, like pathway 78, can be either unidirectional or bidirectional. Any and/or all of signal pathways 74-79 of an extended system can be a part of either a publicly accessible network (e.g., the internet) or an access-controlled network (e.g., corporate, military, institutional) network.

Via an extended airway obstruction correction system 70, a remotely located entity (e.g., doctor, clinician, technician) can monitor the condition of an apparatus 1 in real time, collect operational data over time, monitor an airway condition of a patient, and/or affect changes to the configuration parameters of an apparatus 1. Therefore, it is not necessary for a user who is a patient of a doctor, for example, to sleep in a clinical setting in order for the doctor to collect data on the user's airway condition during normal sleep, or to alter configuration parameters to affect the operation of an apparatus 1. Rather, the user can sleep in their normal, home sleep setting while the doctor remotely monitors the user's airway condition. As such, the data collected by the doctor is more accurate and relevant for effective treatment, since a user is typically more likely to relax and sleep naturally and normally in their home setting than in a clinical setting.

Airway Obstruction Correction Method

Figure 8:
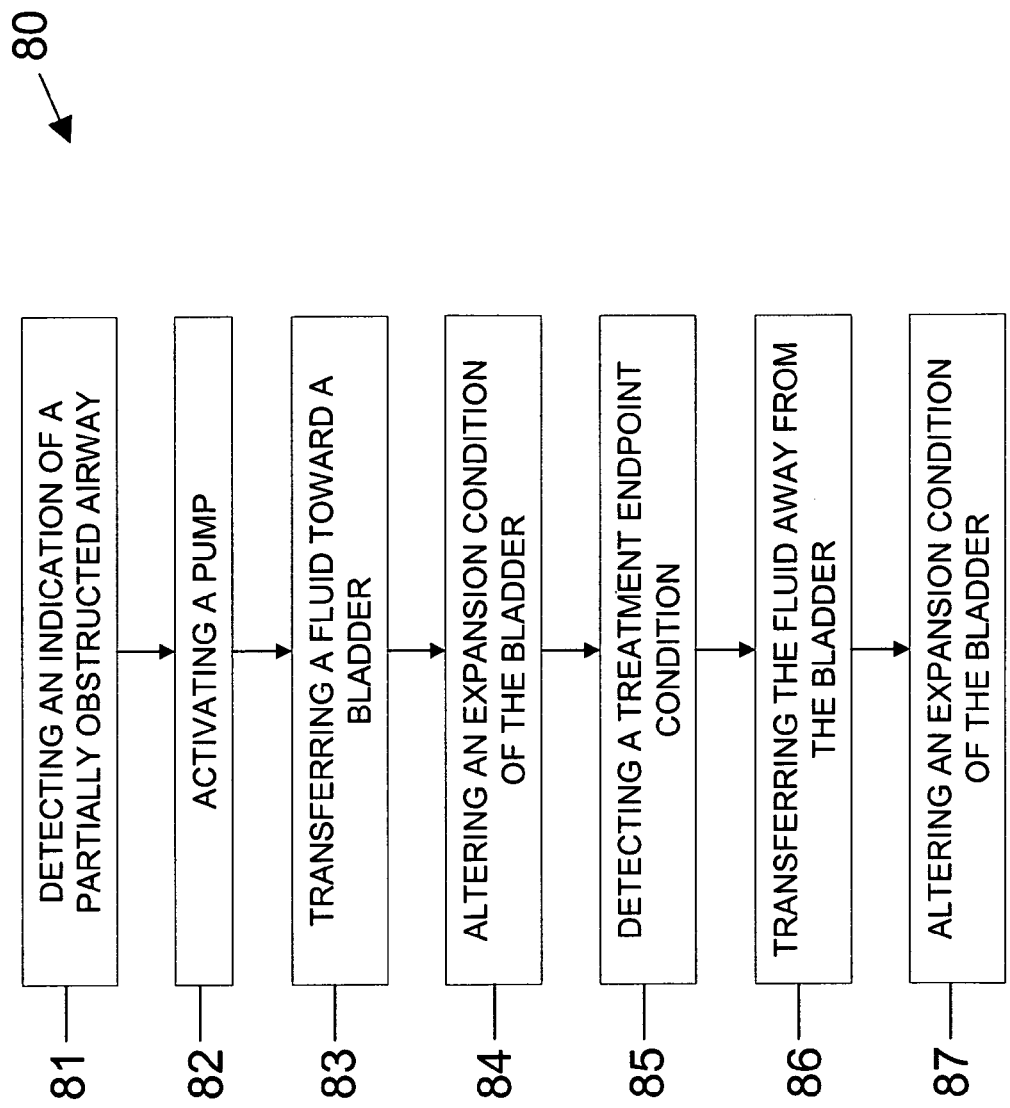
FIG. 8 depicts a method of correcting an airway obstruction in a user by an airway obstruction correction apparatus according to an embodiment of the invention.

An embodiment of an airway obstruction correction method 80 is substantially depicted at FIG. 8, although many variants thereof are conceived within the scope of the invention according to alternative embodiments. The method 80 includes detecting at 81 an indication of a partially obstructed airway, for example by detecting pre-snore or snore sounds, or detecting at a microphone 45 a fully obstructed airway by the cessation of normal breathing sounds. In response to indications corresponding to a trigger condition preset as at least one configuration parameter, a microcontroller transmits an activation signal to a pump 67, and the pump 67 is activated at 82. The pump 67 then transfers fluid from a reservoir 68a toward an elastic bladder at 83.

In response to an increased volume of fluid flowing into the bladder 25, a fluid pressure within a bladder 25 increases and alters an expansion condition of the bladder 25 as indicated at 84. Pumping of the fluid by a pump 67 and the corresponding expansion of the bladder 25 typically continues until a microcontroller 61 detects the presence of an endpoint condition, at 85. Subsequently, the microcontroller 61 terminates an activation signal to the pump 67, and the pump 67 ceases pumping fluid toward the bladder 25. Subsequently, fluid is transferred away from the bladder at 86, and the reduced volume of fluid in the bladder 25 results in a corresponding decrease of fluid pressure in the bladder 25, altering an expansion condition of the bladder at 87.

Fluid may be transferred away from the bladder 25 by any one of or combination of several mechanisms. According to one, the elastic contraction of a bladder membrane 40 is sufficient to force a fluid to exit the bladder and flow through a passage toward a reservoir 68a anytime that a pump 67 ceases pumping a fluid toward the bladder 25. Therefore, an expansion condition of a bladder 25 is primarily influenced by the presence or absence of a pumping action by a pump 67. According to another, a directional pumping action of a pump 67 is altered, causing fluid to be actively pumped from a bladder 25 toward a reservoir 68a. In still another, an overpressure signal from a pressure transducer 47 causes a pressure relief valve 48 to open, allowing fluid to flow away from the bladder 25 and through the pressure relief valve 48.

A treatment endpoint condition can include any one of or combination of conditions. For example, an endpoint condition can be an expiration of a duration of time during which a bladder 25 remained expanded and/or a fluid pressure remained at or above a threshold fluid pressure. An endpoint condition can also arise when an excessive fluid pressure is detected at a pressure transducer 47. Still another endpoint condition can include the detection of sounds indicating restoration of normal breathing (e.g., the absence of sounds of an at least partially obstructed airway) by the user. A failure condition of the microprocessor can also constitute an endpoint condition. For example, if the microcontroller 61 fails to produce an output signal with one or more characteristic of a waveform (e.g., amplitude, frequency) within a range defined by preset configuration parameters, the pump will not operate, and will not convey a fluid toward a bladder 25.

Among the configuration parameters that can be preset, by a doctor of a user for example, are a duration of time for a pump to continue pumping a fluid and/or a minimal interval of time between pump activation events. These, as well as other configuration parameters and/or structural features comprise safety features to prevent injury to a user's auditory canal 21 and/or associated tissues, membranes, bones, and/or other structures, either during normal operation or as a result of operational malfunctions. For example, an embodiment of a control unit 7 can include a watchdog timer configured to reset the microcontroller 61 if an operational function of the microcontroller 61 locks up (fails to properly respond or operate within a preset time limit). Additionally, embodiments including safety features can also help to prevent damage to the apparatus.

Figure 9:
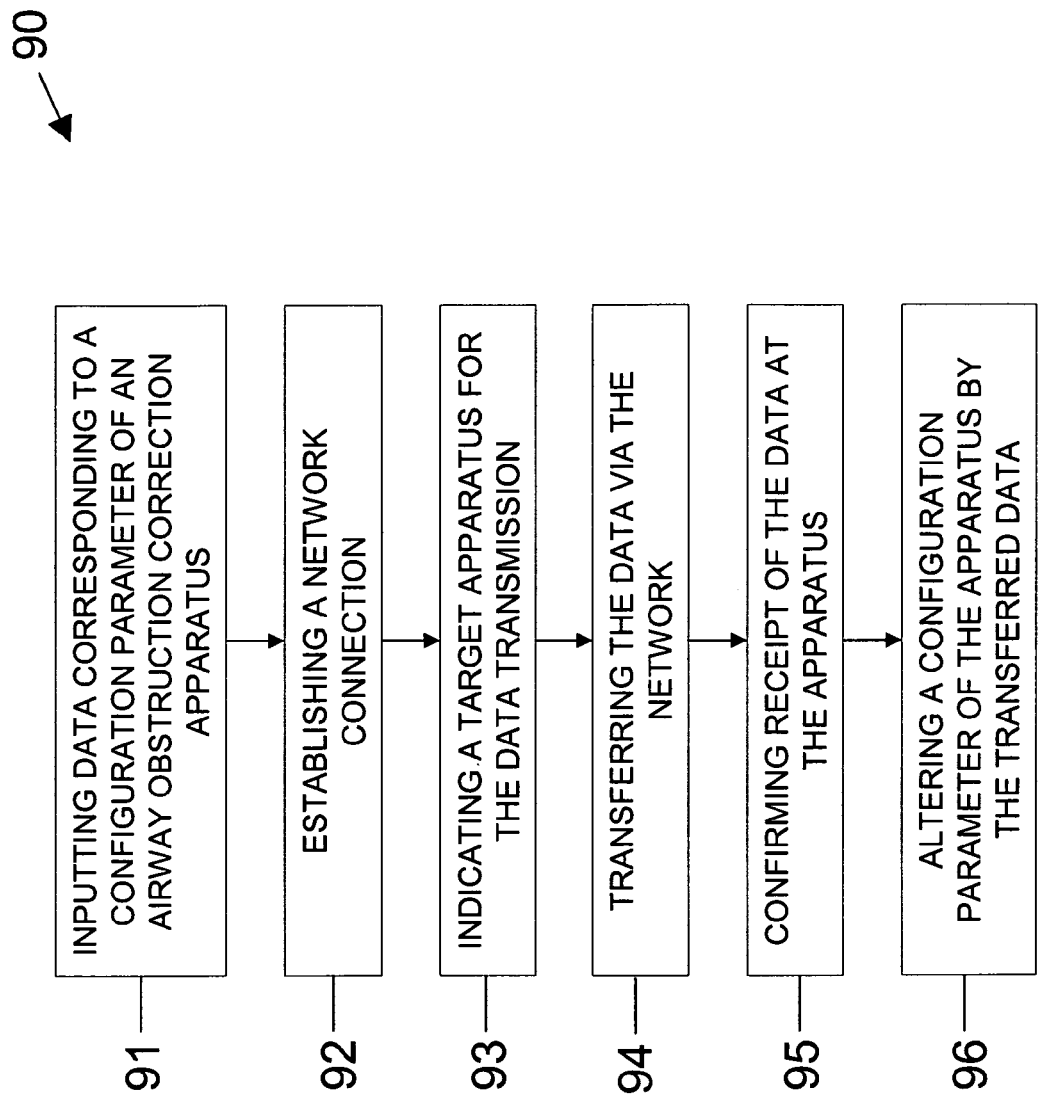
FIG. 9 depicts a method of altering a configuration parameter of an invention by an airway obstruction correction system according to an embodiment of the invention.

With reference to the embodiment depicted in FIG. 9, another method of using an airway obstruction correction apparatus 1 can also include transferring data between a remote device 71 and an apparatus 1 to affect the operation and/or condition of at least one configuration parameter. For example, at 91, a method can include an entity (e.g., a doctor) inputting at a remote computer 71 data corresponding to a configuration parameter of an airway obstruction correction apparatus 1. The entity then establishes a network connection, at 92, between the remote computer 71 and a device 72 configured to receive and re-convey a data-bearing signal. The entity indicates a target apparatus 1 for a data transmission including at least the data corresponding to the configuration parameter, at 93, and then at 94, transfers the data via the network. At 95, following completion of the data transmission, the entity confirms by the remote computer 71 receipt of the data at the target apparatus 1, and at 96, at least one configuration parameter of the target apparatus is altered by the transferred data.

According to alternative embodiments, one or more of the operations depicted in FIGS. 8 and/or 9 may be omitted, one or more additional operations may be added, or the arrangement of at least one operation may be altered relative to at least another operation to alter the sequence of operations. As such, the embodiment of the methods depicted in FIGS. 8 and/or 9 are for illustrative purposes only, and do not limit other methods according to alternative embodiments.

It will be understood that embodiments of the present invention are not limited to the method or detail of construction, fabrication, material, application or use described and illustrated herein. Indeed, any suitable variation of fabrication, use, or application is contemplated as an alternative embodiment, and thus is within the spirit and scope, of the invention.

From the foregoing, those of skill in the art will appreciate that several advantages of the present invention include the following:

Embodiments of the present invention provide a relatively unobtrusive apparatus, wearable by a user occasionally suffering from an obstructed airway during sleep. In contrast with prior art approaches, embodiments of an apparatus according to the invention induce intra-auditory canal pressure to stimulate the physiological response of subconscious jaw adjustment, enabling a user to open their airway without interruption of sleep. Use of an apparatus as conceived and described herein eliminates the need for intrusive surgery, obtrusive and claustrophobic hardware, and several mechanisms of detrimental therapy-induced effects to patients.

Additionally, although occurring while asleep, it is possible that a user can be trained, by use of an embodiment of the present invention, to subconsciously adjust their jaw during sleeping in response to snoring and/or an apnea event. Once so trained, a user could subsequently maintain the beneficial response and benefit of a clear airway through only periodic use of the apparatus. Therefore, the apparatus can be characterized as a airway obstruction correction training and maintenance apparatus.

According to various embodiments, the invention provides several safety features configured to prevent injury to the user or to the apparatus itself due to various apparatus failure conditions. Likewise, injury to a user from repetitive or sustained use, or by improper insertion of the apparatus can also be avoided. Embodiments include an apparatus with custom formed and fitted ear portions, unique to a user's auditory canals, to further enable safe comfortable and effective use by an obstructed airway sufferer.

The described embodiments include a local system enabling a user or other entity to receive and analyze data from the apparatus, and to input and transfer data to the apparatus, including data configured to alter at least one configuration parameter of the apparatus. The local system can include one or more apparatuses, and one or more computing devices, which can be configured for transmission wired and/or wireless signals.

Likewise, an extended system is also enabled by embodiments of the invention, whereby a relatively remote entity can monitor the condition and functioning of both an apparatus and a patient's airway, and can transmit data configured to alter at least one configuration parameter of an apparatus.

It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that the method, system and apparatus of the invention may be implemented by a computer or microcontroller process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. An airway obstruction correction apparatus, comprising:
    an expandable bladder coupled substantially coaxially with a shaft having a longitudinal axis, the bladder and a portion of the shaft configured to fit within at least one of a respective right or left human external auditory canal;
    a pump configured to at least one of expand and contract the bladder with a pumped fluid;
    a microphone coupled with the shaft and configured to be disposed proximate to a user's tympanic membrane during use within the auditory canal;
    a passage operatively coupled with the pump at a first end of the passage, and operatively coupled with the bladder at a second end of the passage, and configured to convey the fluid between the pump and the bladder; and
    a reservoir operatively coupled with the pump and configured to retain a sufficient quantity of the fluid to expand the bladder at least into contact with a surface of the auditory canal.

2. The airway obstruction correction apparatus of claim 1, wherein the microphone is configured to convert audible indications of obstructed breathing to electrical data, and wherein a microcontroller is operatively coupled with the microphone and configured to analyze the data, and the microcontroller is further operatively coupled with the pump and configured to affect an actuation condition of the pump.

3. The airway obstruction correction apparatus of claim 2, further comprising:
    an amplifier operatively coupled with each of the microphone and the microcontroller, and configured to augment data corresponding to the audible indications.

4. The airway obstruction correction apparatus of claim 2, further comprising:
    an analog-to-digital signal converter configured to convert the electrical data from an analog signal to a digital signal.

5. The airway obstruction correction apparatus of claim 2, further comprising:
    a pressure transducer configured to detect a pressure condition of the fluid, and further operatively coupled in electronic communication with the microcontroller.

6. The airway obstruction correction apparatus of claim 2, further comprising:
    at least one of a transmitter and a receiver configured to transfer data between the microcontroller and either or both of a local data processing device and a remote data processing device.

7. The airway obstruction correction apparatus of claim 2, further comprising:
    an indicator means configured to indicate an actuation condition of the microcontroller, a power level condition of a battery, an error condition of the microcontroller, a pressure condition of the fluid, or any combination thereof.

8. The airway obstruction correction apparatus of claim 2, further comprising:
    a power source operatively coupled with at least one of the microcontroller and the pump.

9. The airway obstruction correction apparatus of claim 2, further comprising:
    a tunable audio filter operatively coupled with the microphone and configured to discriminate sounds of an at least partially obstructed airway.

10. The airway obstruction correction apparatus of claim 1, further comprising:
    a retention structure operatively coupled with the shaft and configured to position and retain the bladder within the auditory canal.

11. The airway obstruction correction apparatus of claim 10, further comprising:
    at least one connecting member coupled at a first end thereof with the retention structure and coupled at a second end thereof with the shaft, and configured to enable positional adjustment of the bladder relative to the retention structure and relative to the auditory canal.

12. The airway obstruction correction apparatus of claim 1, further comprising:
    a positioning spacer coupled with the shaft distally relative to the bladder and configured to position and retain the shaft relatively centrally within the auditory canal.

13. The airway obstruction correction apparatus of claim 1, wherein the pump is a piezoelectric pump.

14. The airway obstruction correction apparatus of claim 1, further comprising:
    a pressure relief mechanism operatively coupled with at least one of the passage or the bladder and configured to release fluid when predetermined fluid pressure limits are exceeded.

15. The airway obstruction correction apparatus of claim 1, further comprising:
    an insertion-limiting structure configured to limit an insertion depth of the bladder into the auditory canal.

16. An airway obstruction correction method comprising:
    detecting one or more indications of an at least partially obstructed airway in a sleeping person by a microphone disposed within an auditory canal and proximate to a tympanic membrane of the person;
    activating a pump of an airway obstruction correction apparatus;
    transferring fluids between a reservoir and an expandable bladder through a passage; and
    altering an expansion condition of the bladder within the external auditory canal and affecting a force upon a corresponding surface of the auditory canal.

17. The airway obstruction correction method of claim 16, further comprising:
    contracting the bladder at the occurrence of at least one of, (1) an expiration of a preset duration of time, (2) detection of an indication of a clear airway, or (3) detection of a fault condition in the apparatus.

18. The airway obstruction correction method of claim 17, wherein contracting the bladder includes causing fluid to flow from the bladder toward the reservoir by either or both of reversing a direction of flow induced by the pump and elastically contracting the bladder.

19. The airway obstruction correction method of claim 16, wherein detecting one or more indications of an at least partially obstructed airway includes monitoring the person's audible breathing sounds with the microphone, converting detected sound patterns to data, and processing the data by a microcontroller.

20. The airway obstruction correction method of claim 19, further comprising:
    transferring the data between a microcontroller integrally coupled with the airway obstruction correction device and a non-integrally coupled data processing device.

21. The airway obstruction correction method of claim 16, further comprising:
    deactivating the airway obstruction correction device, including causing a microcontroller integrally coupled with the airway obstruction correction device to first confirm that the bladder is substantially contracted.

22. The airway obstruction correction method of claim 16, further comprising:
    remotely altering a configuration parameter of an airway obstruction correction apparatus.

23. An airway obstruction correction system, comprising:
    an airway obstruction correction means, including:
        an expandable bladder configured to fit within a human external auditory canal,
        a pump configured to transfer a fluid,
        a passage operatively coupled with the pump at a first end of the passage and with the bladder at a second end of the passage and configured to convey the fluid between the pump and the bladder,
        a microphone coupled with the passage at the second end of the passage, wherein the microphone is configured to be disposed proximate to a tympanic membrane within the external auditory canal,
        a reservoir operatively coupled with the pump and configured to contain at least a portion of the fluid, and
        a microcontroller operatively coupled with the pump and configured to affect an activation condition of the pump; and
    a remotely located data processing means configured to at least one of process data received from the airway obstruction correction apparatus and transmit data configured to affect an operational parameter of the airway obstruction correction apparatus.

24. The airway obstruction correction system of claim 23, further comprising:
    a data conveying means operatively coupled with and configured to transfer data between the airway obstruction correction apparatus and the remote data processing means.

25. The airway obstruction correction system, of claim 24, wherein the data conveying means includes one or both of a wireless data transmitting means and a wired data receiving means.

26. The airway obstruction correction system of claim 23, wherein the remotely located data processing means includes a display means configured to visually display at least a portion of the received data, and also including a data input means configured to enable an entity to pre-configure the transmitted data.

* * * * *